United States Patent [19]
Thiele et al.

[11] Patent Number: 6,100,412
[45] Date of Patent: Aug. 8, 2000

[54] PROCESS FOR THE EPOXIDATION OF OLEFINIC COMPOUNDS

[75] Inventors: Georg Thiele, Hanau, Germany; Shane A. Nolan, Atlanta, Ga.; James S. Brown, Atlanta, Ga.; Jie Lu, Atlanta, Ga.; Brandon C. Eason, Atlanta, Ga.; Charles A. Eckert, Atlanta, Ga.; Charles L. Liotta, Atlanta, Ga.

[73] Assignee: Degussa-Huls AG, Frankfurt, Germany

[21] Appl. No.: 09/393,263

[22] Filed: Sep. 10, 1999

[51] Int. Cl.[7] .................... C07D 301/03; C07D 301/02
[52] U.S. Cl. ............... 549/523; 549/518; 549/531; 568/859; 568/860
[58] Field of Search ................................ 549/518, 523, 549/531; 568/859, 860

[56] References Cited

U.S. PATENT DOCUMENTS

| | | | |
|---|---|---|---|
| 4,847,393 | 7/1989 | Langley | 549/523 |
| 5,241,088 | 8/1993 | Meyer et al. | 549/523 |
| 5,525,741 | 6/1996 | Sugita et al. | 549/523 |

*Primary Examiner*—Amelia Owens
*Attorney, Agent, or Firm*—Pillsbury Madison & Sutro LLP

[57] ABSTRACT

A process for the production of an epoxide and/or its corresponding vicinal diol by a reaction of an olefinic compound with hydrogen peroxide, wherein the reaction is performed in the presence of a carbon dioxide phase at a temperature and a pressure above the critical point of carbon dioxide.

5 Claims, No Drawings

PROCESS FOR THE EPOXIDATION OF OLEFINIC COMPOUNDS

The subject of the invention is a process for the preparation of epoxides and/or products derived therefrom during epoxidation by the reaction of an olefinic compound with hydrogen peroxide.

BACKGROUND OF THE INVENTION

Epoxides are important intermediates for the manufacturing of numerous products. They are preferably prepared by the oxidation of the corresponding olefins. It is desirable to use hydrogen peroxide as the oxidant, as it leaves only water after the reaction. However, hydrogen peroxide is not reactive enough and has to be activated for the oxidation of olefins.

A known way of activation is the reaction of hydrogen peroxide with a carboxylic acid to give a peroxycarboxylic acid, which is capable of oxidizing olefins to epoxides. These processes have the disadvantage, that the carboxylic acid, which is used as an auxiliary, has to be separated from the reaction product or discarded with the aqueous effluent after the reaction, which leads to additional cost.

Another known way of activation is the use of a catalyst for the oxygen transfer. These processes carry additional cost for the catalyst. In addition, these catalysts and the transition metals on which they are usually based on tend to pollute the aqueous effluents and have to be removed from the aqueous waste with considerable expenditure.

Both ways of activation also require substantial safety measures, as the decomposition of hydrogen peroxide can liberate molecular oxygen, which can form flammable vapors with the olefin or the usually required solvent. Therefore the gas phase over the reaction mixture has to be inertized.

Thus, it is the object of the present invention to provide a process which does not have the above exhibited disadvantages.

DESCRIPTION OF THE INVENTION

We now found unexpectedly, that olefins can be oxidized with hydrogen peroxide to give epoxides or products derived therefrom, if the reaction is activated by carbon dioxide under certain conditions.

Thus the subject of the invention is a process for the production of an epoxide and/or its corresponding vicinal diol by a reaction of an olefinic compound with hydrogen peroxide, characterized by the fact, that the reaction is performed in the presence of a carbon dioxide phase at a temperature and a pressure above the critical point of carbon dioxide.

According to this invention, the oxidation of olefins is performed in a two phase system, with the first phase containing mainly carbon dioxide and the second phase containing mainly hydrogen peroxide and water.

Poorly water soluble olefins will dissolve mainly in the carbon dioxide phase, water soluble olefins will mainly dissolve in the aqueous phase. Optionally a solvent may be added to influence the partitioning of the olefin between both phases.

Compounds with one or several carbon carbon double bonds, either isolated or conjugated, may be reacted. The olefin can have a linear, branched or cyclic structure and can optionally be substituted. Substituents on the olefin are e.g. alkyl groups, aryl groups or functional groups, such as halogens, hydroxyl groups, ether groups, carbonyl groups, ester groups or carboxyl groups. Substituted olefinic compounds having a substituent oxidizable by hydrogen peroxide can be transformed by the inventive process into compounds having not only an epoxide and/or diol structure but also the said substituent in an oxidized form.

Hydrogen peroxide is used as an aqueous solution having a $H_2O_2$-content of 1 to 90 weight percent, preferably 30 to 70 weight percent. Optionally one or more stabilizers may be present or be added to the hydrogen peroxide, which stabilize hydrogen peroxide in a known manner against decomposition by traces of transition metals.

The molar ratio of hydrogen peroxide to olefinic compound can be chosen within a wide range and usually comprises a range of from 10:1 to 1:20, preferably from 2:1 to 1:10.

The reaction is performed at a temperature and a pressure above the critical temperature and the critical pressure of carbon dioxide. For water insoluble olefins the pressure is chosen high enough to obtain a homogeneous phase from the olefin and the carbon dioxide. The temperature is preferably in the range from 35 to 100° C. and the pressure is preferably in the range from 7.5 to 30.0 MPa.

It is preferred to add a base to the reaction mixture, which forms with carbon dioxide a hydrogencarbonate which is soluble in the aqueous phase. By adding the base both the rate of reaction and the selectivity for the epoxide can be improved. Suitable bases are alkali metal hydroxides, alkali metal carbonates, alkali metal hydrogencarbonates, ammonia and amines. Preferably used are sodium hydroxide, sodium carbonate and sodium hydrogencarbonate. Depending on the olefinic compound to be reacted and the reaction temperature, the base is used in such a quantity to enable the desired effect of increased reactivity and selectivity on one hand but keep the loss of hydrogen peroxide by base catalyzed decomposition low on the other hand.

In the process according to the invention the carbon oxide acts as an activator for hydrogen peroxide and in addition as a solvent. Presumably, under the reaction conditions of the invention a reaction of hydrogen peroxide and carbon dioxide takes place to give a peroxycarbonic acid species, i.e. a compound where the peroxy group of hydrogen peroxide gets bound to the carbon of carbon dioxide. The transfer of oxygen to the olefin probably occurs from this peroxycarbonic acid species and not from hydrogen peroxide. Depending on the reaction conditions, the epoxide may further react to derivatives of the epoxide, particularly to the corresponding diol which is formed by hydrolysis of the epoxide and/or a glycol ether, a reaction product between the said diol and the epoxide.

The process according to this invention allows the oxidation of olefins with hydrogen peroxide without converting hydrogen peroxide into a lower peroxycarboxylic acid in a previous step or using a transition metal catalyst. After the reaction the carbon dioxide can easily be separated as a gas. Since carbon dioxide is not flammable, no inertization is needed to run the reaction safely. By using a sufficient excess of carbon dioxide the reaction can be performed in such a manner, that no flammable mixtures can occur even with an unexpected decomposition of the hydrogen peroxide. Details on practicing the process may be taken from the following examples.

EXAMPLE 1

A 30 ml stainless steel pressure vessel was charged with 6 ml 30 weight percent hydrogen peroxide and 2.3 ml cyclohexene and heated to 40° C. with stirring. Carbon dioxide was added until the pressure reached 12.0 MPa and stirring was continued at 40° C. for 19 h. Then the pressure was lowered to ambient pressure over 1 h and volatile products were absorbed from the outgoing carbon dioxide through a row of several gas wash bottles filled with acetone. The aqueous and organic phases in the reactor and the acetone used for absorption were analyzed for reaction products by gas chromatography. The yield of cyclohexene oxide calculated on the cyclohexene charged was 0.08%.

EXAMPLE 2

Example 1 was repeated, but 70 mg sodium hydrogencarbonate were charged together with the cyclohexene and the hydrogen peroxide. The yield of cyclohexene oxide calculated on the cyclohexene charged was 3.2%.

What is claimed is:

1. A process for the production of at least one member selected from the group consisting of an epoxide and a corresponding vicinal diol thereof by reaction of an olefinic compound with hydrogen peroxide, comprising:

carrying out the reaction in the presence of a carbon dioxide phase at a temperature and a pressure above the critical point of carbon dioxide.

2. The process according to claim 1, comprising:

using the olefinic compound and the hydrogen peroxide in a molar ratio in the range from 10:1 to 1:20.

3. The process according to claim 1, comprising:

carrying out the reaction at a temperature in the range from 35 to 100° C. and a pressure in the range from 7.5 to 30 Mpa.

4. The process according to claim 2, comprising:

carrying out the reaction at a temperature in the range from 35 to 100° C. and a pressure in the range from 7.5 to 30 Mpa.

5. The process according to any one of claims 1 to 4, comprising:

carrying out the reaction in the presence of a catalytically active amount of a base.

* * * * *